(12) United States Patent
Hallasch et al.

(10) Patent No.: US 10,115,190 B2
(45) Date of Patent: Oct. 30, 2018

(54) DETERMINING A MATERIAL TYPE AND/OR A SURFACE CONDITION OF A WORKPIECE

(71) Applicant: TRUMPF Werkzeugmaschinen GmbH + Co. KG, Ditzingen (DE)

(72) Inventors: Dieter Hallasch, Ditzingen (DE); Tim Hesse, Ditzingen (DE); Boris Regaard, Stuttgart (DE); David Schindhelm, Stuttgart (DE)

(73) Assignee: TRUMPF Werkzeugmaschinen GmbH + Co. KG, Ditzingen (DE)

( * ) Notice: Subject to any disclaimer, the term of this patent is extended or adjusted under 35 U.S.C. 154(b) by 75 days.

(21) Appl. No.: 15/394,415

(22) Filed: Dec. 29, 2016

(65) Prior Publication Data

US 2017/0109874 A1 Apr. 20, 2017

Related U.S. Application Data

(63) Continuation of application No. PCT/EP2015/064864, filed on Jun. 30, 2015.

(30) Foreign Application Priority Data

Jul. 1, 2014 (DE) .......... 10 2014 212 682

(51) Int. Cl.
*G06K 9/00* (2006.01)
*G06T 7/00* (2017.01)
(Continued)

(52) U.S. Cl.
CPC ............ *G06T 7/001* (2013.01); *B23K 26/032* (2013.01); *B23K 26/14* (2013.01); *B23K 26/24* (2013.01);
(Continued)

(58) Field of Classification Search
CPC ...... G06T 7/001; B23K 26/60; B23K 23/702; B23K 23/032; B23K 23/14; B23K 23/24;
(Continued)

(56) References Cited

U.S. PATENT DOCUMENTS 5,155,558 A * 10/1992 Tannenbaum ......... G01N 21/57
348/128
6,273,785 B1 * 8/2001 Mulroy .................. B23Q 1/385
451/178
(Continued)

FOREIGN PATENT DOCUMENTS

CN 102981390 3/2013
DE 19846619 A1 4/2000
(Continued)

OTHER PUBLICATIONS

Juptner et al., "Opto-Electronic Sensor for Realtime-Visualization of Laser-Welding Process for Seam Tracking and Adaptive Process Control", Abstract, Laser und Potoelektronik, vol. 22, No. 6, Stuttgart, Germany, 1990, 8 pages.
(Continued)

*Primary Examiner* — Ali Bayat
(74) *Attorney, Agent, or Firm* — Fish & Richardson P.C.

(57) ABSTRACT

This disclosure relates to methods and apparatuses for determining a material type and/or a surface condition of a workpiece. A surface of the workpiece is illuminated with illuminating radiation. At least one image of the illuminated surface is recorded. The material type and/or the surface condition of the workpiece is determined on the basis of a statistical analysis of the at least one image converted into a spatial frequency domain.

22 Claims, 2 Drawing Sheets

(51) Int. Cl.
| | |
|---|---|
| *B23K 26/03* | (2006.01) |
| *B23K 26/32* | (2014.01) |
| *G01B 11/30* | (2006.01) |
| *G01N 33/20* | (2006.01) |
| *G01N 21/55* | (2014.01) |
| *B23K 26/14* | (2014.01) |
| *B23K 26/24* | (2014.01) |
| *B23K 26/38* | (2014.01) |
| *B23K 26/40* | (2014.01) |
| *B23K 26/70* | (2014.01) |
| *B23K 26/60* | (2014.01) |
| *G06K 9/46* | (2006.01) |
| *G06K 9/74* | (2006.01) |
| *G01N 21/86* | (2006.01) |
| *G01N 21/84* | (2006.01) |
| *G01N 21/89* | (2006.01) |

(52) U.S. Cl.
CPC .............. *B23K 26/32* (2013.01); *B23K 26/38* (2013.01); *B23K 26/40* (2013.01); *B23K 26/60* (2015.10); *B23K 26/702* (2015.10); *G01B 11/303* (2013.01); *G01N 21/55* (2013.01); *G01N 33/20* (2013.01); *G06K 9/4661* (2013.01); *G06K 9/748* (2013.01); *G01N 21/86* (2013.01); *G01N 2021/8416* (2013.01); *G01N 2021/8918* (2013.01); *G01N 2201/12* (2013.01); *G06T 2207/20081* (2013.01); *G06T 2207/20084* (2013.01); *G06T 2207/30164* (2013.01)

(58) Field of Classification Search
CPC ...... B23K 23/40; G06K 9/4661; G06K 9/748; G01B 11/303; G01N 21/55
See application file for complete search history.

(56) References Cited

U.S. PATENT DOCUMENTS

| | | |
|---|---|---|
| 7,177,032 B2 | 2/2007 | Lex |
| 7,630,516 B2 | 12/2009 | Lex |
| 8,659,810 B2 | 2/2014 | Joo |
| 2003/0023341 A1* | 1/2003 | Sagawa .............. G05B 19/4093 700/159 |
| 2007/0140799 A1* | 6/2007 | Kumakiri .............. B23B 29/025 407/66 |
| 2012/0188365 A1 | 7/2012 | Stork |
| 2014/0362385 A1* | 12/2014 | Uemura ............. G01B 11/2441 356/511 |

FOREIGN PATENT DOCUMENTS

| | | |
|---|---|---|
| DE | 10324104 | 12/2004 |
| DE | 10339227 | 3/2005 |
| DE | 102007008768 A1 | 8/2008 |
| DE | 102011005907 B3 | 3/2012 |
| WO | WO2010057661 A1 | 5/2010 |
| WO | WO2012126769 A1 | 9/2012 |

OTHER PUBLICATIONS

International Search Report for corresponding PCT Application No. PCT/EP2015/064864, dated Sep. 14, 2015, 6 pages.
Office Action in European Application No. 15734626.3, dated Aug. 8, 2018, 6 pages.
Search Report in Chinese Application No. 201580036324.3, dated Apr. 26, 2018, 4 pages.

* cited by examiner

DETERMINING A MATERIAL TYPE AND/OR A SURFACE CONDITION OF A WORKPIECE

CROSS-REFERENCE TO RELATED APPLICATIONS

This application is a continuation of and claims priority under 35 U.S.C. § 120 to PCT Application No. PCT/EP2015/064864 filed on Jun. 30, 2015, which claims priority to German Application No. 10 2014 212 682.7, filed on Jul. 1, 2014. The entire contents of these priority applications are incorporated herein by reference.

TECHNICAL FIELD

The present invention relates to methods and apparatuses for determining a material property or condition, e.g., a material type and/or a surface condition, of a preferably metallic, in particular plate-shaped, workpiece, and to a computer program product for carrying out the method.

BACKGROUND

During the processing of workpieces on a machine tool, for example during cutting of workpieces by means of a high-energy beam, it is typically necessary to know the material type (for example construction steel, stainless steels, nonferrous metal, etc.) as well as the surface condition (for example oxidation of the surface, roughness, coating of the surface for example with paint or film, etc.) of the workpiece, to suitably adapt processing parameters such as, for example, advance rate, laser power, gas type and gas pressure. The material type or the surface condition of a workpiece to be processed is typically indicated manually by an operator of the machine tool. If the operator indicates to the machine tool a material type or a surface condition that does not correspond to the actual material type to be processed or the surface condition of the workpiece to be processed, this typically leads to an inferior outcome of the processing operation.

German Patent Publication DE 10 2011 005 907 B3 has disclosed a method for determining the reflectivity of a surface, which is illuminated with incident illumination, images of the surface being recorded with different illumination times and determining the bright surface proportion in which a predetermined minimum brightness is achieved in each of the recorded images. From the bright surface proportion determined, as a function of the different exposure times, the variation of the bright surface proportion with the exposure time is determined, and the reflectivity of the surface is determined therefrom to identify and distinguish between highly reflective and matte surfaces.

SUMMARY

Various embodiments disclosed herein provide methods and apparatuses that allow automatic determination of the material type and/or the surface condition of a workpiece.

Certain embodiments provide methods for determining a material property, such as a material type and/or a surface condition, of a workpiece, such as a metallic plate-shaped workpiece. The methods include illuminating a surface of the workpiece with illuminating radiation, recording at least one image of the illuminated surface, and determining or classifying the material type and/or the surface condition of the workpiece on the basis of at least one image converted into the spatial frequency domain, typically on the basis of a statistical analysis of the at least one image converted into the spatial frequency domain. The illumination of the surface of the workpiece is typically bright-field incident illumination, in which the illuminating radiation is reflected directly back into the observation direction from the surface of the workpiece.

In certain implementations of the invention, automated classification of different material types, or materials, and/or different surface conditions of the workpiece are carried out—generally in an automated fashion—to select processing parameters and/or processing technologies that are optimized, or particularly highly suitable, for processing the workpiece in the machine tool. The determination of the material type and/or surface condition of the workpiece is carried out on the basis of the analysis of the at least one recorded image of the surface of the workpiece that has been converted into the spatial frequency domain. In the spatial frequency domain, characteristic structures of the surface of the workpiece, in particular light/dark structures, can be identified or analyzed particularly well. It has, in particular, been found that the spatial frequency domain of the recorded image of a given surface differs significantly from the spatial frequency domain of other surfaces, so that it is particularly advantageous to distinguish between different material types and/or surface conditions on the basis of an image, converted into the spatial frequency domain, of the surface of the workpiece.

In various implementations, the material type and/or the surface condition of the workpiece are determined on the basis of an anisotropy of the frequency distribution of the spatial frequencies and/or on the basis of at least one direction-independent property (typically a direction-independent measure of dispersion) of the frequency distribution of the spatial frequencies of the image converted into the spatial frequency domain. The statistical analysis of the frequency distribution of the spatial frequencies of the image converted into the spatial frequency domain may be carried out with the aid of known methods from image processing, for example by calculation of the two-dimensional spatial moments, in which the ellipticity of the spatial frequency distribution is calculated, which represents a measure of the anisotropy of the frequency distribution of the spatial frequencies in the surface structure, the spatial moments giving the maximum and minimum radii of the circumscribing ellipse of the standard deviation, i.e. the major axes of the standard deviation of the frequency distribution of the spatial frequencies. As a direction-independent property of the frequency distribution of the frequencies in the spatial frequency domain, it is for example possible to use a scalar measure of dispersion, for example the (scalar) standard deviation or the variance of the frequency distribution. Both the direction-independent property and the anisotropy in the spatial frequency domain, i.e., the direction-dependent spatial frequency domain, which may for example be described by the characteristic quantities of maximum radius and minimum radius of the circumscribing ellipse (spatial moments) of the frequency distribution, may be used as discriminating criteria between different material types or different surface conditions. In particular, these two discriminating criteria may be used together with the reflectance as a third discriminating criterion to determine the material type and/or to determine the surface condition.

In addition to determining the material type and/or the surface condition on the basis of the image converted into the spatial frequency domain, for the determination of the material type or surface condition of the workpiece it is also possible to take the reflectance of the surface of the workpiece for the illuminating radiation into account. The reflectance may in this case be determined for one wavelength, for example for the wavelength of the illuminating radiation, i.e., as an absolute reflectance. It is, however, also possible to determine the reflectance of the surface of the workpiece for a plurality of different wavelengths of the illuminating radiation, and to put the respective reflectances into relation with one another (relative reflection) to determine the surface condition and/or the material type. It is also possible to determine the maximum, minimum, and average reflectances of the surface. To distinguish between different material types and/or surface conditions, in addition to the discriminating criteria obtained from the analysis of the image converted into the spatial frequency domain, the (absolute or relative) reflectance may be used as a further discriminating criterion.

In certain implementations, the reflectance, the anisotropy of the spatial frequencies, and/or the frequency distribution of the spatial frequencies are compared with reference data for different material types and/or surface conditions to determine the material type and/or the surface condition of the workpiece. The reference data for the reflectance, the anisotropy of the spatial frequencies, and/or the frequency distribution of the spatial frequencies for different material types and/or surface conditions may be stored in a database. Based upon the comparison of the values of the aforementioned discriminating criteria determined during the analysis of the image with respective reference data, it is possible to determine that material type or surface condition that comes closest to the values determined during the analysis of the image.

In various implementations, the comparison is carried out with the aid of a learning system, in particular with the aid of an (artificial) neural network. A learning system may be trained with reference data for the anisotropy of the spatial frequencies, the frequency distribution of the spatial frequencies and/or the reflectance of different known material types and/or surface conditions during a learning phase. If the values of the anisotropy, the frequency distribution and/or the reflectance, determined during the analysis of the image of the workpiece, are provided as input quantities to such a trained neural network, the neural network automatically assigns to these input quantities that material type and/or surface condition that comes closest to the given input quantities. Instead of a learning system, other methods may be used for the comparison, for example so-called template matching, in which small subregions of an image are compared with predetermined image constituents (templates), SAD (sum of absolute difference), etc.

In certain implementations, the material type is determined from a group that comprises construction steel, stainless steel and nonferrous metals, i.e., the workpiece is classified as construction steel, stainless steel or as nonferrous metal. The classification of the material type need not necessarily be restricted to allocation to one of the three types of workpieces mentioned above. Rather, distinction may optionally be made between different types of construction steels and/or determination of a respective nonferrous metal, for example copper, aluminum, etc., may be carried out in the material class of nonferrous metals.

In particular implementations, the determination of the surface condition comprises the detection of a rolled surface of the workpiece. Since rolled metal sheets have a groove structure dependent on the rolling direction, with the aid of the anisotropy of the spatial frequencies of the image converted, or transformed, into the spatial frequency domain, it is possible to identify whether the workpiece is a rolled workpiece. In particular, a rolled workpiece may in this case be distinguished from a workpiece produced for example by a compression molding method, or a workpiece coated with paint, film or the like, since such workpieces do not generally have a preferential direction that can be identified as anisotropy in the spatial frequency domain. In addition, or as an alternative to the rolling direction of the workpiece, it is also possible to determine other surface properties, for example the roughness or the oxidation of the surface.

In certain implementations, an exposure time and/or an illumination intensity is/are adapted to the reflectance of the surface of the workpiece during the recording of the image. The illumination intensity or the exposure time is in these cases selected in such a way that the recorded image has a contrast that is as high as possible. Based on the exposure time or illumination intensity required to produce a high contrast, the reflectance of the surface may be deduced indirectly, i.e. it is not necessary to determine the reflectance of the surface by means of a separate reflectivity measurement.

In various implementations, the determination of the material type and/or the surface condition comprises the formation of an average value from a number of between 10 and 1000 images converted into the spatial frequency domain. Determination of the material type and/or of the surface condition of the workpiece based on averaged image sequences is generally improved significantly compared with determination based on a single image. Analysis of the spatial frequency range of an individual image often already allows clear discrimination between different material types or surface conditions.

In particular implementations, the illumination of the surface of the workpiece is carried out with laser radiation as the illuminating radiation, i.e., with illuminating radiation that has (at least) one discrete wavelength. The illumination source of the illuminating device may, for example, be a diode laser that generates illuminating radiation at a wavelength of for example 660 nm, 808 nm, 915 nm, or 980 nm. The illumination of the surface should as far as possible be carried out homogeneously. The illuminating radiation may, for example, be homogenized by means of a fiber or a glass rod. The illumination of the surface is preferably carried out as incident light illumination, since a high contrast is generated in incident light illumination by the natural roughness of the surface of the workpiece. Illuminating radiation with different wavelengths can be used to determine the reflectance or the reflection intensity of the surface at different wavelengths, and to compare the reflection intensities. As described above, the reflectance at different wavelengths may be used as a further discriminating criterion between different material types and/or surface conditions.

In certain implementations, the illuminating radiation is irradiated onto the surface coaxially with a high-energy beam for processing the workpiece. During processing of the workpiece with a high-energy beam, for example with a laser beam, for example during laser beam cutting or during laser beam welding, or with a plasma beam, it has been found favorable for the illumination of the surface of the workpiece and/or the observation of the surface of the workpiece to take place coaxially with the high-energy beam. In this way, a minimal interference contour is produced and the determination of the material type and/or the surface condition may be carried out both immediately before the processing and during the processing (i.e., during primary processing time). The coupling of the illuminating radiation in and the coupling of the observation beam path out from the beam path of the high-energy beam may, for example, be carried out by local (for example lateral) coupling in or out, or using a semitransparent mirror (dichroite).

In various implementations, the methods include determining of at least one processing parameter for the processing of the workpiece as a function of the material type and/or the surface condition. As described above, the processing parameters of the processing operation, for example of a laser welding process or of a laser cutting process, such as, for example, the advance rate, the laser power, the type of gas delivered to the workpiece as an auxiliary gas or as a cutting gas, and the gas pressure of such a gas, may be optimized on the basis of the material type and/or the surface condition determined in the manner described above. Depending on the material type and/or the surface condition of the workpiece, a selection of suitable processing technologies for processing the workpiece may also be made, for example the selection of a laser suitable for the processing or of a suitable laser wavelength.

Certain embodiments of the invention also relate to a computer program product, such as a non-transitory computer-readable storage device storing computer executable instructions, which if executed by a machine controller of a laser processing machine causes the machine controller to carry out all steps of the method described. The controller can include a data processing unit configured as a control device, a regulating device or an evaluation device, which is part of a processing machine for the workpiece. It may, however, also be an external device, for example a PC, which is connected to the processing machine to exchange data.

Further embodiments of the invention relate to an apparatus of the type mentioned in the introduction, comprising: an illuminating device for generating illuminating radiation for illuminating a surface of the workpiece, an image acquisition device for recording at least one image of the illuminated surface of the workpiece, and an evaluation device that is configured, or programmed, to determine the material type and/or the surface condition of the workpiece on the basis of the at least one image converted into the spatial frequency domain.

As described above in connection with the methods, automated determination of the material type and/or the surface condition of the workpiece may be carried out with the aid of the apparatus. The apparatus may for example be configured as a processing head, in particular as a laser processing head. In this case, the evaluation device is typically integrated into the processing head. The apparatus may also be a processing machine, in particular a laser processing machine. In this case, the evaluation device is typically arranged separately from the processing head.

In certain embodiments, the image acquisition device is configured to record the at least one image by means of an observation beam path extending through a focusing lens for focusing a high-energy beam onto the workpiece. The image acquisition device is arranged, or configured, in such a way that the observation beam path extends through the focusing lens, through which a high-energy beam, for example a laser beam or a plasma beam, which is used for processing a workpiece, also passes. For the implementation of such an observation beam path, the image acquisition device may be assigned imaging optics having one or more suitably positioned optical elements, for example in the form of one or more lenses.

In various implementations, the image acquisition device is configured to record the at least one image from an observation direction coaxial with the principal axis of the focusing lens. In the ideal case, the beam axis of the high-energy beam coincides with the principal axis of the focusing lens, which extends centrally through the focusing lens, i.e., the high-energy beam passes centrally through the focusing lens. By coaxial observation of the plane workpiece surface, which is typically oriented perpendicularly to the principal axis of the focusing lens, direction-independent observation can be carried out, which is favorable for determination of the material type and/or the surface condition of the workpiece.

In certain implementations, the illuminating device is configured to illuminate the surface of the workpiece through the focusing lens, preferably coaxially with the principal axis of the focusing lens. As described above, incident light illumination of the surface of the workpiece is favorable since a high contrast is generated in this case because of the natural roughness of the workpiece surface.

In particular implementations, the illuminating device comprises at least one laser, in particular a diode laser, or a light-emitting diode, as the illumination source. For determination of the material type and/or the surface condition of the workpiece, it has been found favorable for the illumination to be carried out with at least one discrete wavelength and with a homogeneous illumination source having a high beam quality, for example with a diode laser. The coupling of the illuminating radiation into the beam path of the high-energy beam may, for example, be carried out laterally or by means of a semi-transmissive mirror.

In various implementations, the evaluation device is configured, or programmed, to determine the material type and/or the surface condition of the workpiece based on an anisotropy of the frequency distribution of the spatial frequencies and/or at least one direction-independent property of the frequency distribution of the spatial frequencies of the image converted into the spatial frequency domain. As described above in connection with the method, the direction-dependent spatial frequency domain or the anisotropy of the spatial frequencies, and the at least one direction-independent property of the frequency distribution of the spatial frequencies, may be calculated with the aid of known image processing methods, for example by calculating the spatial moments.

In certain implementations, the evaluation device is configured additionally to take the reflectance of the surface of the workpiece into account to determine the material type and/or surface condition of the workpiece. As described above, the reflectance of the surface, optionally measured for different wavelengths of the illuminating radiation, may be used as an additional discriminating criterion to be able to distinguish between different material types and/or surface conditions.

In particular implementations, the evaluation device is configured, or programmed, to compare the reflectance, the anisotropy of the spatial frequencies and/or the frequency distribution of the spatial frequencies with reference data for different material types and/or surface conditions to determine the material type and/or the surface condition. The reference data for the reflectance, the anisotropy of the spatial frequencies and/or the frequency distribution of the spatial frequencies for different material types and/or surface conditions may be stored in a database. On the basis of a comparison of the three discriminating criteria with the respective reference data, it is possible to determine that material type or surface condition that comes closest to the values determined during the analysis of the image. The evaluation device may, in particular, be configured to carry out the comparison by means of a self-learning system, for example by means of an (artificial) neural network. It is, however, also possible to carry out the comparison, or the search for similar parameters in the database, with the aid of a conventional minimization function, for example by minimizing the least squares of the errors.

Other advantages of the invention may be found in the description and the drawing. Likewise, the features mentioned above and those yet to be described below may each be used independently or several may be used together in any desired combination. The embodiments shown and described are not to be understood as an exhaustive list, but rather are of exemplary nature for the description of the invention.

DETAILED DESCRIPTION

Figure 1:
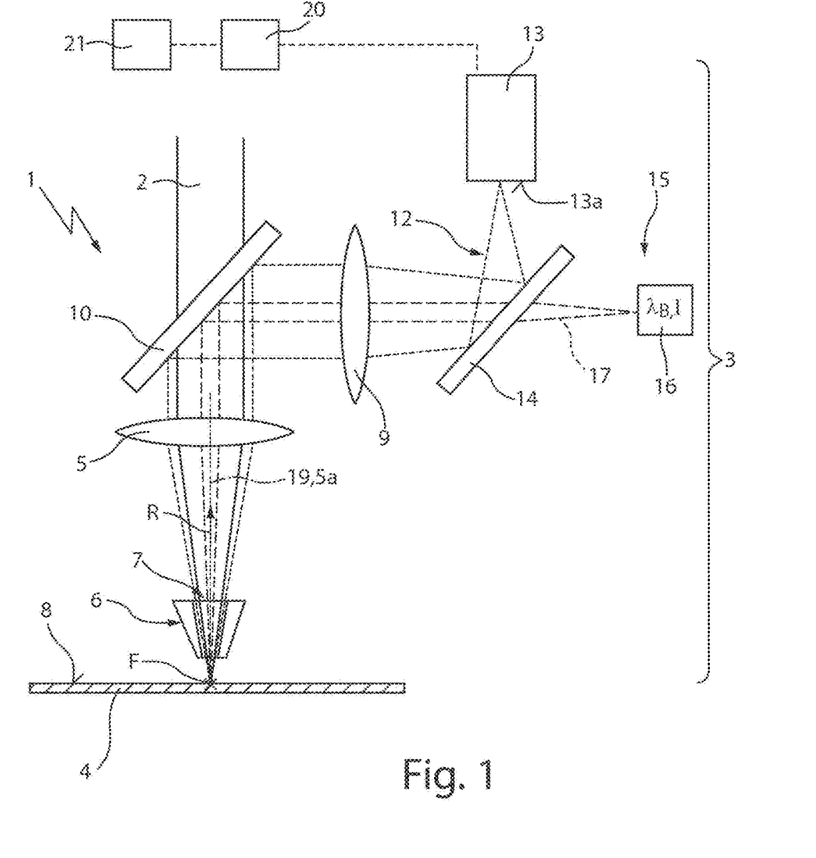
FIG. 1 shows a schematic representation of an example of an embodiment of a laser processing machine for determining a material type and/or a surface condition of a workpiece to be processed.

FIG. 1 shows an exemplary structure of an apparatus in the form of a laser processing machine 1, which comprises a processing head 3 for focusing a laser beam 2 onto a workpiece 4 lying at a distance from the processing head 3. In the example shown, the laser beam 2 is generated by a $CO_2$ laser. As an alternative, the laser beam 2 may, for example, be generated by a solid-state laser. The laser beam 2 is focused onto the workpiece 4 by means of a focusing device in the form of a focusing lens 5 to carry out workpiece processing on the workpiece 4, for example in the form of a laser welding process or a laser cutting process.

The processing head 3 further comprises a processing nozzle 6, wherein, in the example shown, the focusing lens 5 focuses the laser beam 2 onto the workpiece 4 through the processing nozzle 6, or more precisely through an opening 7 on the inner side of the processing nozzle 6, specifically onto a workpiece surface 8, formed on the upper side of the workpiece 4, which the laser beam 2 strikes at a focal position F in the example shown.

FIG. 1 also shows a semitransparent mirror 10, through which the laser beam 2 arriving from a beam guide passes and strikes the focusing lens 5. At the semitransparent mirror 10, observation radiation (for example in the visible wavelength range) of an observation beam path 12 represented by dashes in FIG. 1 is deflected and travels through a further lens 9 and a further semitransparent mirror 14 onto an image acquisition device 13 in the form of a camera. The image acquisition device 13 may be a high-resolution camera, which may, in particular embodiments, be configured as a high-speed camera. In the example shown, the recording of images by the image acquisition device 13 takes place in the near-infrared (NIR) wavelength range. Recording of images in the VIS or UV ranges is also possible. In the example shown in FIG. 1, a filter may be arranged in front of the image acquisition device 13 if further radiation or wavelength components are intended to be excluded from the recording by the image acquisition device 13. The filter may, for example, be configured as a narrowband bandpass filter.

The further lens 9 is used together with the focusing lens 5 as imaging optics for imaging the workpiece surface 8 onto a detector surface 13a of the camera 13. The imaging optics, or the camera 13, are arranged in such a way that the observation beam path 12 extends coaxially with the laser beam axis 19 represented by dots and dashes in FIG. 1, or the continuation thereof. Since the laser beam axis 19 coincides with the principal axis 5a of the focusing lens 5, the observation of the workpiece surface 8, or the recording of the image of the workpiece surface 8, takes place in an observation direction R coaxial with the principal axis 5a of the focusing lens 5 and with the longitudinal axis of the typically rotationally symmetrical processing nozzle 6, and therefore direction-independent.

The processing head 3 further comprises an illuminating device 15, which is used to illuminate the surface 8, lying at a distance from the processing head 3, of the workpiece 4. The illuminating device 15 comprises an illumination source 16, which generates an illuminating beam 17 represented by dashes in FIG. 1. In particular, a diode laser, or optionally an LED, for example with a wavelength of 660 nm, 808 nm, 915 nm, or 980 nm, may be provided as the illumination source 16. The illumination beam 17 passes through the further semitransparent mirror 14 as well as the further lens 9, and deviates at the semitransparent mirror 10 in the direction of the focusing lens 5. The illuminating beam 17 is aligned coaxially with the laser beam 2, or the principal axis 5a of the focusing lens 5, so that the illumination beam 17 passes through the opening 7 of the processing nozzle 6 and illuminates the surface 8 of the workpiece 4.

A method by which the material type and/or the surface condition of the surface 8 of the workpiece 4 may be determined with the aid of the laser processing machine 1 shown in FIG. 1 will be described below. It is to be understood that the determination of the material type and/or the surface condition of the workpiece 4 need not necessarily take place during the workpiece processing shown in FIG. 1, but that it may in particular also take place shortly before the start of the workpiece processing.

Figure 2A:
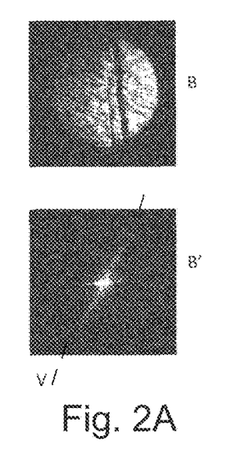
FIGS. 2A, 2B, and 2C show representations of three images in the spatial domain (B), and three images converted into the spatial frequency domain (B'), of a workpiece surface of a plate-shaped workpiece.
Figure 2B:
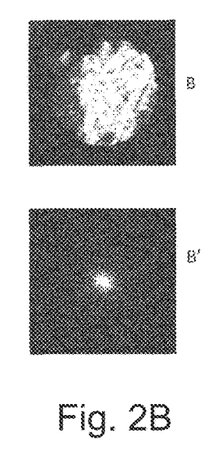
Figure 2C:
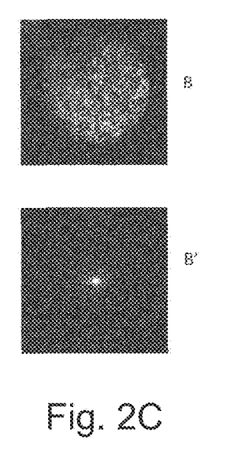

The top portion of FIGS. 2A, 2B, and 2C, respectively represent an image B, recorded by the camera 13, of the surface 8 of a workpiece 4. A circular edge contour of the processing nozzle 6 forms a boundary of the observation region through which the surface 8 of the workpiece 4 can be observed. The section of the workpiece surface 8 that can be seen through the opening 7 in each case has a different characteristic surface condition.

The workpiece 4 whose surface 8 is represented in the images B shown in FIGS. 2A, 2B, and 2C is in all three cases a rolled stainless steel sheet. In FIG. 2A, the workpiece 4 is a blank stainless steel sheet, i.e., the image B is an image of the blank surface 8 of the stainless steel sheet. In the image B shown in FIG. 2B, the stainless steel sheet is coated with an uncuttable film, and in the image B shown in FIG. 2C the stainless steel sheet is coated with a cuttable film.

To be able to distinguish better between the different surface conditions (blank surface or different coatings) on the basis of the images B shown in FIGS. 2A, 2B, and 2C, the images B shown in FIGS. 2A, 2B, and 2C of the surface 8 of the workpiece 4 are converted into the spatial frequency domain (i.e., Fourier-transformed). The bottom portion of FIGS. 2A, 2B, and 2C show the images B' that represent the respective images B converted into the spatial frequency domain. In the image B', shown in FIG. 2A, converted into the spatial frequency domain, an anisotropy of the spatial frequencies, or a direction-dependent spatial frequency domain, with a preferential direction V indicated by dashes, can clearly be seen, this being attributable to the groove structure of the stainless steel sheet rolled along a rolling direction. The images B', represented in FIG. 2B and FIG. 2C, converted into the spatial frequency domain, are essentially isotropic in the spatial frequency domain, but differ in the dispersion of the values of the frequency distribution of the spatial frequencies, i.e., the image B', shown in FIG. 2B, converted into the spatial frequency domain, has a larger dispersion of the spatial frequencies, while the image B', shown in FIG. 2C, converted into the spatial frequency domain, is concentrated more strongly around the center at low spatial frequencies. The differences between the frequency distributions represented in FIG. 2B and in FIG. 2C can be described well by a direction-dependent (scalar) measure of dispersion for frequency distributions, for example by the mean absolute deviation of the individual values of the frequency distribution from the mean value of the frequency distribution, or by the (direction-independent) standard deviation or variance.

The surface condition of the workpieces 4 can therefore be determined with the aid of the three images B', shown in FIGS. 2A, 2B, and 2C, converted into the spatial frequency domain, by calculating a measure of dispersion of the anisotropy of the spatial frequencies of the frequency distribution and/or at least one direction-independent measure of dispersion of the frequency distribution of the spatial frequencies. Such a calculation of the measure of dispersion may be carried out with the aid of methods known from image processing, for example by calculating the spatial moments of the image B' converted into the spatial frequency domain. The spatial moments form a two-dimensional measure of dispersion, from which the anisotropy of the frequency distribution is obtained. For such a calculation, an evaluation device 20, which is connected by signal technology to the camera 13, is provided in the laser processing machine 1. The evaluation device 20 may be integrated into the laser processing machine 1, for example in the form of a PC or the like, and connected by signal technology to a control or regulating device 21.

To determine the surface condition of the workpiece 4 on the basis of the anisotropy of the frequency distribution of the spatial frequencies and/or on the basis of at least one direction-independent property, typically a measure of dispersion, of the frequency distribution of the spatial frequencies of a respective image B' converted into the spatial frequency domain, the evaluation device 20 is configured to compare the values obtained during the analysis of the respective image B' with reference data or reference values for different surface conditions, which are typically stored in a database to which the evaluation device 20 has access. For the comparison, a learning system, for example in the form of an artificial neural network, may be implemented in the evaluation device 20. Instead of a learning system, the evaluation device 20 may use other methods for the comparison, for example so-called template matching, in which small subregions of an image are compared with predetermined image constituents (templates), sum of absolute difference, (SAD), etc. It is, however, also possible for the evaluation device 20 to carry out the comparison, or the search for similar parameters in the database, with the aid of a conventional minimization function, for example by minimizing the least squares of the errors.

In addition to the differentiation or classification of workpieces 4 in terms of their surface condition, the evaluation device 20 may also determine different material types. To this end, reference data or reference values for different material types may be stored in the database and likewise compared with the values respectively determined during the analysis for the scalar or direction-dependent properties of the frequency distribution of the spatial frequencies.

In addition to the two discriminating criteria described above for different materials and/or different surface conditions, the reflectance of the surface 8 of the workpiece 4 may be used as a further discriminating criterion. To this end, for example, the exposure time $t_A$ (cf., FIGS. 3A, 3B, 3C, and 3D), with which the camera 13 records a respective image B, and/or the illumination intensity I (cf., FIG. 1) may be adapted until the image B has a sufficient contrast.

On the basis of the adapted exposure time $t_A$ and the adapted illumination intensity I, it is possible to deduce the reflectance of the surface 8 of the workpiece 4, which provides a first indicator of the material type and/or the surface condition of the workpiece 4. The reflectance may also be determined at a plurality of wavelengths of the illuminating radiation 17 to improve the classification of different material types or surface conditions. In this case, the reflectances determined for different wavelengths of the illuminating radiation 17 may be put into relation with one another (relative reflection) to determine the surface condition and/or the material type.

Figure 3A:
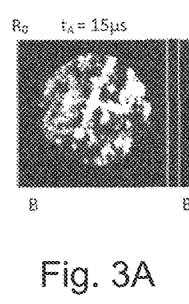
FIGS. 3A, 3B, 3C, and 3D show representations of four images of workpiece surfaces of workpieces of different construction steel types.
Figure 3B:
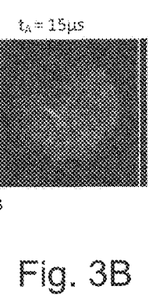
Figure 3C:
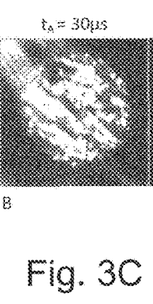
Figure 3D:
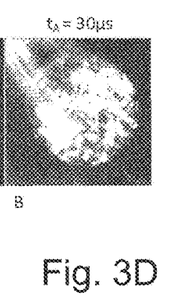

FIGS. 3A, 3B, 3C, and 3D show four images B, recorded by the camera 13, of different construction steel types, the images B shown in FIGS. 3A and 3B having been recorded with an exposure time $t_A$ of 15 µs and the images B shown in FIGS. 3C and 3D having been recorded with an exposure time $t_A$ of 30 µs. Differentiation between the construction steel types is possible by means of the different reflectances $R_O$ and with the aid of the groove structure, which may be analyzed with the aid of the images, not represented in FIGS. 3A, 3B, 3C, and 3D, converted into the spatial frequency domain, of the surface 8 of the workpiece 4.

In the manner described above, in particular the material types construction steel, stainless steel and nonferrous metals can be distinguished from one another, it also being possible to distinguish between different nonferrous metals and different construction steel types. Different from what was described in connection with FIGS. 2A, 2B, and 2C and FIGS. 3A, 3B, 3C, and 3D, instead of a single image converted into the spatial frequency domain, it is favorable to form a (pixelwise) average value from a multiplicity of images recorded in chronological succession, for example between 10 and 1000 images B' converted into the spatial frequency range, and to carry out the determination of the material type and/or the surface condition on the basis of this average value. The average value is in this case used for the comparison with the respective reference data. It may possibly be favorable to determine an average value from a multiplicity of images recorded in chronological succession for the determination of the reflectance as well.

Depending on the material type and/or surface condition determined in the manner described above, processing parameters of the processing operation, in the present example a laser welding process or a laser cutting process, may be selected suitably, for example the advance rate, the laser power, the type of gas delivered to the workpiece as an auxiliary gas or as a cutting gas, and its gas pressure. The selection of the processing parameters may be carried out in an automated fashion in the control and/or regulating device 21, which for this purpose can access a database. Optionally, selection of suitable processing technologies, for example the selection of a laser source suitable for the processing, if it is possible to choose in the laser processing machine 1 between a plurality of laser sources for generating the laser beam 2, may also take place in the control and/or regulating device 21.

By the automated detection or determination of the material type and the surface condition, it is possible to avoid error sources in the manual input of the material type by an operator. Destruction of the processing machine by back-reflection of the laser beam 2 on highly reflective materials may also be avoided. Automatic optimization of the processing parameters may also be carried out, in which case, for example, automatic pretreatment of film-coated workpieces may be carried out. The illuminating device 15 and the image acquisition device 13 may also be used advantageously for measuring or determining other measurement quantities relevant to the processing operation.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method for determining a material property of a workpiece, the method comprising:
    illuminating a surface of the workpiece with illuminating radiation;
    recording at least one image of the illuminated surface;
    converting the at least one image in a spatial frequency domain; and
    determining the material property comprising at least one of a material type and a surface condition of the workpiece based on a statistical analysis of the at least one image converted into the spatial frequency domain, wherein at least one of the material type and the surface condition of the workpiece are determined on the basis of at least one of an anisotropy of the frequency distribution of the spatial frequencies and at least one direction-independent property of the frequency distribution of the spatial frequencies of the image converted into the spatial frequency domain.

2. The method of claim 1, wherein the reflectance (Ro) of the surface of the workpiece is additionally taken into account during the determination of at least one of the material type and the surface condition of the workpiece.

3. The method of claim 1, wherein at least one of the reflectance (Ro), the anisotropy, and the frequency distribution of the spatial frequencies are compared with reference data for at least one of different material types and surface conditions to determine at least one of the material type and the surface condition.

4. The method of claim 3, wherein the comparison is carried out with the aid of a learning system.

5. The method of claim 1, wherein the material type is determined from a group comprising: construction steel, stainless steel, and nonferrous metals.

6. The method of claim 1, wherein determining the surface condition comprises detecting a rolled surface of the workpiece.

7. The method of claim 1, wherein at least one of an exposure time ($t_A$) and an illumination intensity (I) is adapted to the reflectance ($R_O$) of the surface of the workpiece during the recording of the image.

8. The method of claim 1, wherein determining at least one of the material type and the surface condition comprises forming an average value from a number of between 10 and 1000 images converted into the spatial frequency domain.

9. The method of claim 1, wherein illuminating the surface of the workpiece is carried out with laser radiation as the illuminating radiation.

10. The method of claim 1, further comprising irradiating the illuminating radiation onto the surface coaxially with a high-energy beam for processing the workpiece.

11. The method of claim 1, further comprising determining at least one processing parameter for the processing of the workpiece as a function of at least one of the material type and the surface condition.

12. The method of claim 1, wherein recording at least one image of the illuminated surface comprises detecting illuminating radiation reflected directly back in the observation direction from the surface of the workpiece.

13. A non-transitory computer-readable storage device storing computer executable instructions for determining a material property of a workpiece, which if executed by a machine controller of a laser processing machine causes the machine controller to:
    illuminate a surface of the workpiece with illuminating radiation;
    record at least one image of the illuminated surface;
    convert the at least one image in a spatial frequency domain;
    determine at least one of a material type and a surface condition of the workpiece based on a statistical analysis of the at least one image converted into the spatial frequency domain; and
    control at least one processing parameter of the laser processing machine during a machining process conducted on the workpiece based on the at least one material type and the surface condition determined.

14. An apparatus for determining a material property of a workpiece, comprising:
    an illuminating device comprising an illumination source for generating illuminating radiation for illuminating a surface of the workpiece;
    an image acquisition device comprising a camera for recording at least one image of the illuminated surface of the workpiece; and
    a programmable evaluation device for determining at least one of a material type and a surface condition of the workpiece on the basis of the at least one image converted into the spatial frequency domain, wherein the programmable evaluation device is configured to determine at least one of the material type and the surface condition of the workpiece on the basis of at least one of an anisotropy of the frequency distribution of the spatial frequencies and at least one direction-independent property of the frequency distribution of the spatial frequencies of the image converted into the spatial frequency domain.

15. The apparatus of claim 14, wherein the image acquisition device is configured to record the at least one image (B) by means of an observation beam path extending through a focusing lens for focusing a high-energy beam onto the workpiece.

16. The apparatus of claim 15, wherein the image acquisition device is configured to record the at least one image (B) from an observation direction (R) coaxial with the principal axis of the focusing lens.

17. The apparatus of claim 15, wherein the illuminating device is configured to illuminate the surface of the workpiece through the focusing lens, preferably coaxially with the principal axis of the focusing lens.

18. The apparatus of claim 14, wherein the illuminating device comprises at least one of a laser or a light-emitting diode, as the illumination source.

19. The apparatus of claim 14, wherein the programmable evaluation device is configured additionally to take a reflectance (Ro) of the surface of the workpiece into account to determine at least one of the material type and the surface condition of the workpiece.

20. The apparatus of claim 14, wherein the programmable evaluation device is configured to determine at least one of the material type and the surface condition of the workpiece on the basis of at least one of an anisotropy of the frequency distribution of the spatial frequencies and at least one direction-independent property of the frequency distribution of the spatial frequencies of the image converted into the spatial frequency domain.

21. The apparatus of claim 20, wherein the programmable evaluation device is configured to compare at least one of a reflectance (Ro), the anisotropy of the frequency distribution of the spatial frequencies, and the frequency distribution of the spatial frequencies with reference data for at least one of different material types and surface conditions to determine at least one of the material type and the surface condition.

22. A method for determining a material property of a workpiece, the method comprising:
    illuminating a surface of the workpiece with illuminating radiation;
    recording at least one image of the illuminated surface;
    converting the at least one image in a spatial frequency domain; and
    determining the material property comprising at least one of a material type and a surface condition of the workpiece based on a statistical analysis of the at least one image converted into the spatial frequency domain, wherein determining at least one of the material type and the surface condition comprises forming an average value from a number of between 10 and 1000 images converted into the spatial frequency domain.

\* \* \* \* \*

UNITED STATES PATENT AND TRADEMARK OFFICE
CERTIFICATE OF CORRECTION

PATENT NO. : 10,115,190 B2
APPLICATION NO. : 15/394415
DATED : October 30, 2018
INVENTOR(S) : Dieter Hallasch et al.

Page 1 of 1

It is certified that error appears in the above-identified patent and that said Letters Patent is hereby corrected as shown below:

In the Claims

Column 11
Line 44, in Claim 2, delete "(Ro)" and insert -- ($R_o$) --
Line 49, in Claim 3, delete "(Ro)," and insert -- ($R_o$), --

Column 13
Line 6, in Claim 19, delete "(Ro)" and insert -- ($R_o$) --
Line 19, in Claim 21, delete "(Ro)," and insert -- ($R_o$), --

Signed and Sealed this
Twenty-sixth Day of February, 2019

Andrei Iancu
*Director of the United States Patent and Trademark Office*